United States Patent [19]

Morgan et al.

[11] Patent Number: 5,507,786
[45] Date of Patent: Apr. 16, 1996

[54] SYSTEM AND METHOD FOR MEASURING AND STORING PARAMETRIC DATA PERTAINING TO OPERATING CHARACTERISTICS OF AN IMPLANTABLE MEDICAL DEVICE

[75] Inventors: Wayne A. Morgan, Granada Hills; Brian M. Mann, Beverly Hills, both of Calif.

[73] Assignee: Pacesetter, Inc., Sylmar, Calif.

[21] Appl. No.: 227,838

[22] Filed: Apr. 14, 1994

[51] Int. Cl.$^6$ .................................................. A61N 1/37
[52] U.S. Cl. ............................................................. 607/27
[58] Field of Search ............................... 607/27, 28, 29, 607/32

[56] References Cited

U.S. PATENT DOCUMENTS

| | | | |
|---|---|---|---|
| 4,231,027 | 10/1980 | Mann et al. | 607/29 |
| 4,345,603 | 8/1982 | Schulman | 128/419 PT |
| 4,596,255 | 6/1986 | Snell et al. | 128/419 PT |
| 4,791,936 | 12/1988 | Snell et al. | 128/697 |
| 4,825,869 | 5/1989 | Sasmor et al. | 607/27 |
| 4,899,750 | 2/1990 | Ekwall | 128/419 PG |
| 5,012,411 | 4/1991 | Policastro et al. | 364/413.06 |
| 5,063,928 | 12/1991 | Grevis et al. | 128/419 D |
| 5,127,404 | 7/1992 | Wyborny et al. | 607/32 |
| 5,137,021 | 8/1992 | Wayne et al. | 128/419 PT |

FOREIGN PATENT DOCUMENTS 0392032  10/1990  European Pat. Off. ............... 607/32

*Primary Examiner*—William E. Kamm
*Attorney, Agent, or Firm*—Lisa P. Weinberg

[57] ABSTRACT

A system and method for measuring and storing parametric data pertaining to the operating characteristics of an implantable medical device are provided. The parametric data may include the impedance of a lead that is attached to a patient's heart, and the internal impedance of a battery used to power the implantable medical device. The parametric data may be measured and stored at predetermined time intervals, as indicated by a clock provided within the implantable medical device. In addition, the parametric data measurements may be synchronized with the occurrence of a cardiac event, such as the application of a stimulation pulse to the patient's heart. A plurality of measurements for each type of parametric data may be stored, so that when the parametric data are later retrieved and displayed on an external programmer/analyzer, trends in the data can be readily observed.

26 Claims, 3 Drawing Sheets

SYSTEM AND METHOD FOR MEASURING AND STORING PARAMETRIC DATA PERTAINING TO OPERATING CHARACTERISTICS OF AN IMPLANTABLE MEDICAL DEVICE

BACKGROUND OF THE INVENTION

The present invention relates to implantable medical devices. More particularly, the invention relates to implantable medical devices that can measure and store parametric data pertaining to operating characteristics of the device, so that later, when a medical practitioner performs a follow-up examination of a patient, the stored parametric data can be retrieved to determine if the device must be repaired or replaced.

Implantable medical devices have become widely used for the diagnosis and treatment of a variety of medical conditions. Some implantable medical devices (known as "implantable cardiac stimulating devices") are designed to monitor and stimulate cardiac tissue of patients who suffer from cardiac arrhythmias. One type of implantable cardiac stimulating device (known as a "pacemaker") is commonly used to treat bradycardia—a condition in which the patient cannot maintain a physiologically acceptable heart rhythm. These devices deliver low energy electrical pulses to the cardiac tissue to establish a regular heart rhythm at a physiologically acceptable rate.

The earliest pacemakers operated asynchronously at a fixed rate (i.e., without regard to physiological need). Thus, if the patient's intrinsic heart rate happened to be about normal for a period of time, the fixed-rate pacemaker would continue to deliver pacing pulses, thereby wasting limited energy reserves. Also, fixed-rate pacemakers were unable to adjust the patient's heart rate in accordance with increased (or decreased) physical exertion. This had the effect of limiting the kinds of activities that a bradycardia patient could engage in, because the fixed-rate pacemaker could not elevate the patient's heart rate to a level that would meet the increased metabolic demands resulting from physical activity. Also, fixed-rate pacemakers occasionally caused discomfort during sleep and rest because, while most people experience a decreased heart rate during these periods, the heart rates of bradycardia patients were held at the fixed rate.

Subsequent advances in pacemaker technology addressed the above-mentioned difficulties related to fixed-rate pacemakers. For example, demand pacemakers include a sensing function to sense the patient's natural cardiac rhythm. When the patient's natural rhythm falls below a predetermined rate, the demand pacemaker delivers pacing pulses. Otherwise, the demand pacemaker inhibits delivery of the pacing pulses, thereby conserving energy. Sensing is typically accomplished by monitoring the patient's intracardiac electrogram (IEGM), and in particular, by counting the number of R-waves which appear in the IEGM over time. However, recent advances have included the ability to directly measure the mechanical activity of the patient's cardiac tissue, as described in the copending, commonly-assigned U.S. patent application Ser. No. 08/091,636, filed Jul. 14, 1993, entitled "Implantable Leads Incorporating Cardiac Wall Motion Sensors and Method of Fabrication and a System and Method for Detecting Cardiac Arrhythmias Using a Cardiac Wall Motion Sensor Signal."

Rate-responsive pacemakers represent another major advance over the above-described fixed-rate pacemakers. Rate-responsive pacemakers include the ability to monitor an indicator of physical activity, and to vary the pacing rate in accordance with the measured level of activity. A variety of indicators have been used to determine whether, and to what extent, the patient is engaged in physical activity. For example, U.S. Pat. No. 4,712,555 (Thornander et al.), which is hereby incorporated by reference in its entirety, describes a rate-responsive pacemaker that uses a physiologic sensor that measures the depolarization time interval between an atrial stimulation pulse and the responsive atrial or ventricular depolarization. The measured time interval serves as an indicator of physiologic need. The time interval between a ventricular stimulation pulse and the resultant ventricular depolarization may also be used as a physiologic indicator. As another illustration, U.S. Pat. No. 4,940,052 (Mann et al.), which is also incorporated by reference in its entirety, describes a rate-responsive pacemaker that uses a piezoelectric transducer as a physiologic sensor. Accelerometers have also been proposed as physiologic sensors, as described in the copending, commonly-assigned U.S. patent applications Ser. No. 08/059,698, filed May 10, 1993, entitled "Miniature Hybrid-Mountable Accelerometer-Based Physical Activity Sensor for a Rate-Responsive Pacemaker and Method of Fabrication" and Ser. No. 08/091,850, filed Jul. 14, 1993, entitled "Rate-Responsive Implantable Stimulation Device Having a Miniature Hybrid-Mountable Accelerometer-Based Sensor and Method of Fabrication."

Other types of implantable cardiac stimulating devices have become increasingly important for the treatment of cardiac arrhythmias other than bradycardia. For example, implantable cardioverters and defibrillators are used to treat patients who are susceptible to recurrent episodes of ventricular tachycardia or fibrillation. Ventricular tachycardia is characterized by an abnormally high heart rate, perhaps up to 200 beats per minute. To terminate this type of arrhythmia, a cardioverter may deliver a cardioversion shock to the cardiac tissue. Cardioversion shocks typically have a much higher energy content than pacing pulses—on the order of about 2 joules to about 5 joules. But it should also be noted that modern pacemakers can be programmed to deliver pacing pulses in a sequence that is known to interrupt tachycardia, such devices being referred to as "antitachycardia pacemakers."

Fibrillation is the most severe cardiac arrythmia. Although often categorized as a type of tachycardia, it is different in the sense that it is difficult, and sometimes impossible, to distinguish individual heartbeats during fibrillation—whereas in classic tachycardia, each R-wave is typically discernable. When the patient's heart fibrillates, it quivers chaotically, and it thereby does not properly fill with and subsequently eject blood. To terminate this arrhythmia, a defibrillator may deliver a high energy shock to the cardiac tissue—on the order of about 10 joules to about 40 joules.

Implantable cardiac stimulating devices which deliver multiple forms of therapy are also known. Such devices are useful for bradycardia patients who are also susceptible to episodes of ventricular tachycardia or fibrillation. These devices may provide "tiered therapy," in which the type of therapy applied (e.g., bradycardia pacing pulses, antitachycardia pacing pulses, cardioversion shocks or defibrillation shocks) is determined in accordance with the type of cardiac arrhythmia detected—with more aggressive therapies being applied in response to more severe arrhythmias. And if a less aggressive therapy fails to interrupt an arrhythmia episode after a predetermined period of time or number of attempts, tiered therapy devices can heighten the level of therapy applied.

Despite the functional differences among the above-described types of implantable cardiac stimulating devices, they are similar in several respects. For example, the typical device includes pulse generating circuitry and a power supply (i.e., a battery) disposed within a bio-compatible housing. The device is usually implanted beneath the skin on the patient's chest, although other suitable locations may be selected.

Stimulation pulses are usually delivered to the cardiac tissue through at least one stimulation electrode disposed within a lead that is connected between the implantable cardiac stimulating device and the cardiac tissue. Catheter-type leads which are transvenously guided from the device to the cardiac tissue are most frequently used; however, other types of leads, such as epicardial patches, may also be used.

After a cardiac stimulating device is implanted in the patient, a medical practitioner will typically perform periodic follow-up examinations to evaluate the performance of the device. This evaluation is typically accomplished through the use of an external programmer/analyzer which has the ability to telemetrically communicate with the implantable cardiac stimulating device. Using the programmer/analyzer, the medical practitioner can send instructions to the implantable cardiac stimulating device which cause the device to operate in a different way. For example, the medical practitioner can telemetrically increase the resting heart rate maintained by a pacemaker if the patient has experienced episodes of lightheadedness during rest.

The medical practitioner can also use the programmer/analyzer to transmit commands which cause the implantable cardiac stimulating device to take parametric data measurements. As used herein, the term "parametric data" refers to information pertaining to the operating characteristics of the implantable cardiac stimulating device. By causing the device to take such measurements and then evaluating the results, the medical practitioner can determine whether the device is functioning properly, or whether repair or replacement is necessary.

Lead integrity is an operating characteristic that is commonly evaluated during follow-up examinations. Since the leads are implanted, they are subject to stresses caused by patient mobility, bodily fluids, and the like, and as a result, they may deteriorate. Indeed, one condition commonly encountered in pacemaker patients is known as "twiddler's syndrome." These patients absentmindedly manipulate the device implanted beneath the skin, thereby occasionally causing lead damage as the leads twist and turn with the device.

To evaluate lead integrity, the medical practitioner generally directs the implantable cardiac stimulating device to measure the lead impedance. This parametric data measurement indicates whether the lead connection between the implantable cardiac stimulating device and the patient's cardiac tissue remains uncompromised. Lead impedances of about 400 Ω to about 750 Ω are typical.

An excessively low lead impedance measurement suggests that the insulation on the lead has deteriorated, causing an undesirable short circuit to the surrounding tissue (other than the targeted cardiac tissue). A short circuit may cause the stimulation pulses to be discharged to the surrounding tissue instead of the cardiac tissue, thereby rendering the stimulation pulses less effective, or perhaps ineffective. In addition, a short circuit may lead to a rapid depletion of energy reserves from the battery.

A high lead impedance measurement indicates that the lead may have fractured. This open circuit condition also prevents the stimulation pulses from reaching their intended destination. Thus, if the lead impedance falls outside the expected range, a surgical procedure to repair or replace the lead may be warranted. Lead impedance may be derived from two other parametric data measurements taken by the device—pulse voltage and pulse current.

Another operating characteristic that is closely monitored during follow-up visits is battery life. Although most implantable cardiac stimulating devices are assigned recommended replacement times by the manufacturer, there may be situations under which the battery drains at an unexpectedly high rate. To determine remaining battery life, the medical practitioner can telemetrically direct the device to measure the internal impedance of the battery (internal battery impedance is known to increase as the battery depletes). When the battery is nearing the end of its useful life, the internal battery impedance may increase much more rapidly than would otherwise be expected. This parametric data measurement may be derived from two other parametric data measurements taken by the device—battery voltage and battery current.

Although the approaches described above for taking parametric data measurements during follow-up visits have been useful, they have been limited in the sense that they have not provided a convenient way to take such measurements between follow-up visits. In some circumstances, this could leave the medical practitioner without sufficient information to make an informed judgement about the current operating condition of the implantable cardiac stimulating device. For example, there are some situations where a partial lead fracture may only intermittently exhibit itself. The lead impedance may appear normal most of the time but occasionally, the partial lead fracture may cause a lead impedance fluctuation. Unless the medical practitioner happens to request a lead impedance measurement at the time of the lead impedance fluctuation (which means the patient happens to be visiting the medical practitioner at that time), there will be no indication of the partial lead fracture.

Also, there are times when the condition of the implantable cardiac stimulating device is better understood by evaluating trends in the parametric data measurements. For example, as mentioned above, the internal battery impedance rapidly increases near the end of its useful life. Therefore, by observing a recent trend of internal battery impedance measurements, one can quickly determine whether or not the implantable cardiac stimulating device should be replaced. But in order to evaluate trends in the data, it is necessary to take frequent measurements—and frequent measurements are impractical using the above-described approaches because follow-up visits are relatively rare. In addition, comparing current parametric data measurements to earlier measurements can be cumbersome when the above-described approaches are used, because the prior data must be retrieved from a source other than programmer/analyzer, such as a file cabinet or a separate computer system. And further, the above-described approaches do not conveniently allow for statistical calculations to be performed based on parametric data measurements taken over an extended period of time.

One cardiac stimulating device that can measure lead impedance is described in the commonly-assigned U.S. Pat. No. 4,899,750 (Ekwall), which is hereby incorporated by reference in its entirety. The Ekwall patent describes a device in which lead impedance is determined by measuring the change in the voltage on a discharge capacitor during the application of a pacing pulse. The system in Ekwall maintains a running average of the lead impedance measurements. If a current lead impedance measurement differs from the running average by more than a threshold amount for three consecutive pulses, then a counter is incremented. A medical practitioner can use the counter reading to evaluate whether the lead needs to be repaired or replaced. However, it is not possible for a medical practitioner using the Ekwall system to determine whether there is a trend in the lead impedance measurements that is a cause for concern—because the individual measurements are not retained.

It would therefore be desirable to be able to provide a medical practitioner with parametric data measurements that are taken at times other than during follow-up visits, so that the medical practitioner can better evaluate intermittent variations and trends in the measurements.

SUMMARY OF THE INVENTION

In accordance with the present invention, a system and method for measuring and storing parametric data pertaining to operating characteristics of an implantable medical device are provided. The present invention may be advantageously applied in the context of implantable medical devices which deliver life-sustaining stimulation pulses to targeted tissue. These devices may include implantable cardiac stimulating devices such as pacemakers, cardioverters, and defibrillators, as well as combination devices which provide multiple forms of therapy for the treatment of cardiac arrhythmias.

The system of the present invention includes circuitry provided within the implantable medical device, which is used to acquire and store parametric data at times which are deemed appropriate for a particular application. Unlike prior approaches that have been used to acquire parametric data, the present invention allows for the acquisition and storage of parametric data between follow-up visits. Thus, the medical practitioner is advantageously provided with far more information than simply that which can be collected during follow-up visits. This provides the medical practitioner with a better understanding of how the implantable medical device is operating—especially with respect to operating characteristics that may exhibit intermittent variations, or in situations where trends in the parametric data measurements are particularly revealing.

Many different types of parametric data measurements can be taken and stored in accordance with the principles of the present invention. Certain types of data may be particularly important in the implantable cardiac stimulating device context—for example, pulse voltage and pulse current (from which lead impedance can be derived) and battery current and battery voltage (from which internal battery impedance can be calculated). As explained above, lead impedance measurements are useful for determining when lead integrity has been compromised, whereas internal battery impedance is suggestive of remaining battery life. These parametric data measurements, when taken on a regular basis, can alert the medical practitioner to problems (such as a partial lead fracture) which would be difficult to detect if the measurements were taken less frequently (i.e., only during follow-up visits). Of course, the types of parametric data that are measured will vary in accordance with the needs of a particular application. For instance, the types of parametric data measured within an implantable diagnostic device (i.e., a device without stimulation capability) or an implantable drug delivery system may differ greatly from the types of data described above in connection with implantable cardiac stimulating devices.

Parametric data measurements may be taken and stored in accordance with the present invention at predetermined intervals or when selected event criteria are met. For some types of parametric data, it may be desirable to take measurements daily, weekly, or perhaps even monthly. To accomplish this, the present invention provides timing circuitry which generates interrupts at the selected intervals to cause a microcontroller within the implantable device to initiate the parametric data measurements.

For some types of parametric data which are preferably measured at regular intervals, it may desirable to deviate the measurement time slightly from the time that the timing circuitry generates an interrupt, in order to synchronize the measurement with a cardiac event. This would typically be the case for lead impedance measurements, which are usually taken during the delivery of stimulation pulses to the cardiac tissue. In such situations, the present invention delays the measurement until a time that is more conducive to taking the measurement. For example, if the interrupt is generated between a pair of successive pacing pulses, the lead impedance measurement is taken during the second pacing pulse.

Parametric data measurements taken in accordance with the principles of the present invention are stored in a memory device for later review by the medical practitioner. More precisely, during a follow-up visit, the medical practitioner can use a programmer/analyzer to telemetrically retrieve the stored parametric data collected since the last follow-up visit. Preferably, a plurality of measurements for each type of parametric data are stored, so that when the data are later retrieved and displayed on the programmer/analyzer, trends in the data can be readily observed. For example, if the internal battery impedance is measured several times between follow-up visits, when the internal battery impedance measurements are retrieved, the medical practitioner can observe whether the battery is being depleted at a constant rate or whether the battery has recently been depleted at an accelerated rate.

In some situations, memory constraints may limit the number of parametric data measurements that can be stored in an internal memory device. Accordingly, the present invention also provides for the consolidated storage of selected types of parametric data through the use of statistical functions such as mean, variance, minimum value, maximum value, and other functions which may be appropriate for a particular application. The statistical results can also be telemetrically transmitted to the programmer/analyzer for review by the medical practitioner. Of course, if the individual parametric data measurements are stored (as described above) the statistics can be computed by the programmer/analyzer at the medical practitioner's convenience.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENT

For purposes of illustration, the present invention is described in the context of an implantable cardiac stimulating device, and even more particularly, in the context of an implantable rate-responsive pacemaker. It should be understood, however, that these principles may be applied, without departing from the spirit of the invention, to other types of implantable medical devices including cardioverters, defibrillators, and devices which perform only diagnostic functions.

Figure 1:
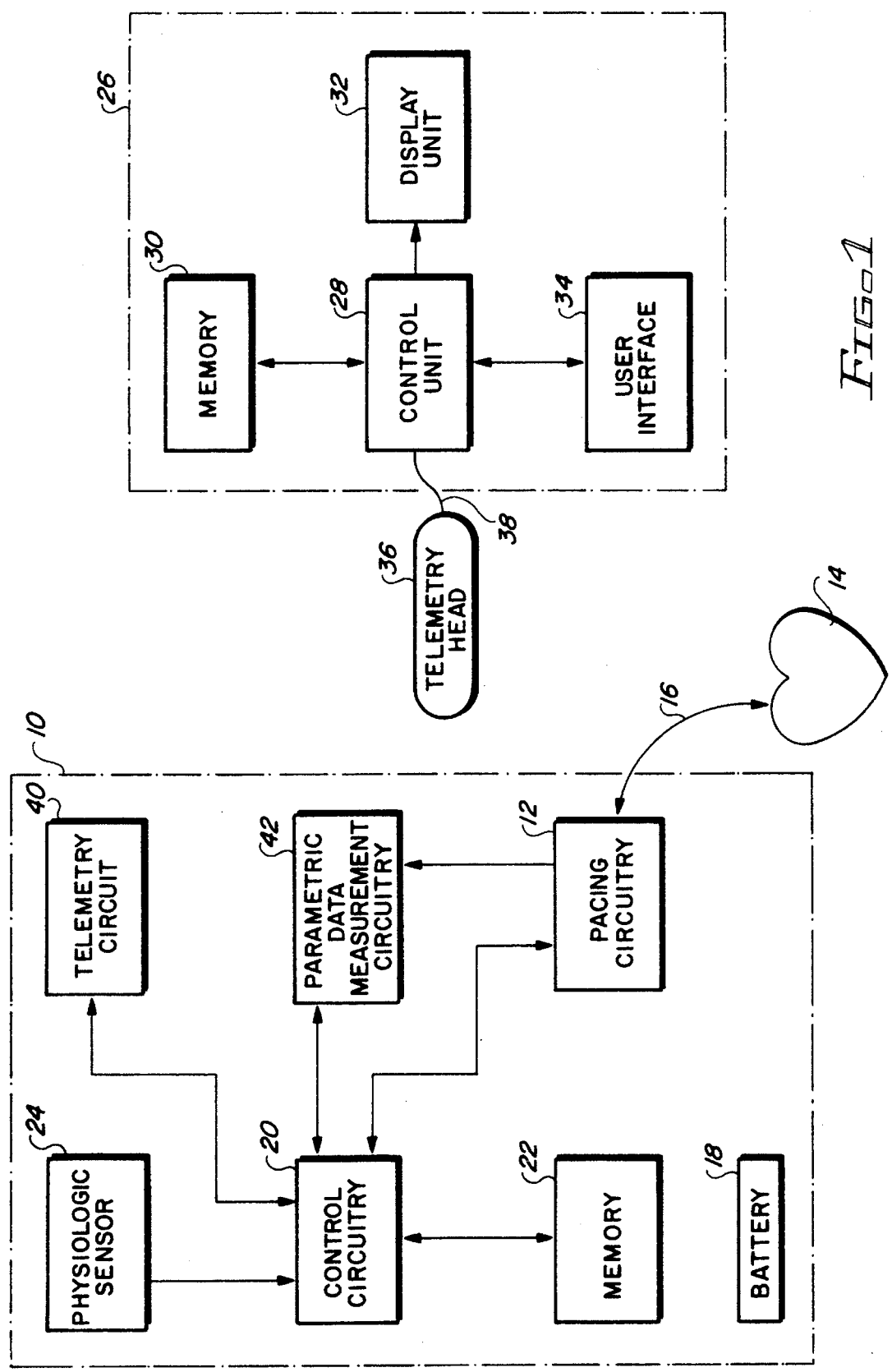
FIG. 1 is a simplified block diagram depicting an implantable cardiac stimulating device and an associated programmer/analyzer, the implantable cardiac stimulating device having the capability of acquiring and storing parametric data in accordance with the principles of the present invention.

Referring first to FIG. 1, an implantable cardiac stimulating device 10 is depicted in a simplified form to illustrate the basic principles of the present invention. The implantable cardiac stimulating device 10 includes pacing circuitry 12 which generates stimulation pulses that are delivered to the patient's heart 14 through a lead system 16. In FIG. 1, the lead system 16 is depicted as a single line coupling the pacing circuitry 12 to the heart 14, but it should be understood that the lead system 16 may include more than one lead if, for example the implantable cardiac stimulating device 10 is a dual-chamber pacemaker.

With certain exceptions described below, the pacing circuitry 12 may be provided by a conventional programmable pacemaker chip. Such pacemaker chips typically include electronics (described below) for regulating the delivery of stimulation pulses to the heart 14 from a pulse generator (described below) that is also provided by the pacemaker chip. The pulse generator of the pacing circuitry 12 is powered by a long-life battery 18. (For clarity, the connections to the battery 18 are not shown in FIG. 1, but it should be understood that the battery 18 is coupled to the pacing circuitry 12, as well as other power consuming components within the implantable cardiac stimulating device 10.) The pacing circuitry 12 typically includes circuitry (described below) for sensing and amplifying the patient's IEGM which is received via the lead system 16 when the pacing circuitry 12 is not delivering a stimulation pulse. When the implantable cardiac stimulating device 10 is operating as a demand pacemaker, the sensed IEGM is used by the pacing circuitry 12 to inhibit delivery of stimulation pulses when the patient's heart rate is physiologically acceptable.

Although the pacing circuitry 12 can operate autonomously for delivering stimulation pulses to the heart 14, additional control circuitry 20 is often provided for enhancing the therapeutic capabilities of the implantable cardiac stimulating device 10. The control circuitry 10 typically includes a microcontroller (described below) which executes program instructions stored in a memory 22. One common type of enhanced capability that may be provided through the use of the control circuitry 20 is rate-responsive pacing. To illustrate, the implantable cardiac stimulating device 10 is shown to include a physiologic sensor 24 which generates a signal representative of the level of activity that the patient is engaged in at any particular time. (One suitable activity sensor is described in the above-mentioned U.S. patent application Ser. No. 08/091,636, filed Jul. 14, 1993.) The control circuitry 20 receives the activity signal and computes a heart rate appropriate for the current level of physical activity. The control circuitry 20 provides a signal representative of the computed heart rate to the pacing circuitry 12 which then adjusts its output to accommodate the current level of activity.

Therapies provided by the implantable cardiac stimulating device 10 may be modified by a medical practitioner through the use of an external programmer/analyzer 26. The programmer/analyzer 26 is typically an interactive device that includes a control unit 28 (such as a microprocessor), a memory 30, a display unit 32 (such as a video monitor), and a user interface 34 (such as a keyboard, digitizer, or pointing device). The medical practitioner enters commands via the user interface 34, which are electronically processed by the control unit 28, and then transmitted to the implantable cardiac stimulating device 10 through a telemetry head 36. The telemetry head 36 is connected to the programmer/analyzer 26 with a cable 38—the cable 38 being long enough to allow the telemetry head 36 to be placed on the patient's chest during a follow-up visit.

Commands transmitted by the telemetry head 36 are received by the implantable cardiac stimulating device 10 through telemetry circuitry 40. Many different kinds of commands can be transmitted to the implantable cardiac stimulating device 10—a simple illustration would be a command to turn the physiologic sensor 24 off, which would cause the pacing circuitry 12 to maintain the patient's heart rate at a fixed rate (instead of a rate based on physical activity level). And the communication link between the telemetry head 36 and the telemetry circuitry 40 is bi-directional—so not only can the implantable cardiac stimulating device 10 receive commands, it can also transmit information (such as a signal representative of the patient's IEGM) to the programmer/analyzer 26. The transmitted information can be reviewed by the medical practitioner on the display unit 32.

With a minimal amount of additional circuitry, the present invention provides a significant enhancement to the implantable cardiac stimulating device 10—through which parametric data pertaining to the operating characteristics of the implantable cardiac stimulating device 10 may be acquired and stored between follow-up visits. Advantageously, the present invention exploits the functionality of many of the above-described components commonly found in known implantable cardiac stimulating devices (i.e., the pacing circuitry 12, the control circuitry 20, the memory 22, and the telemetry circuitry 40). This is an important aspect of the invention, because the patient's comfort may be undesirably sacrificed to some extent if the size of the implantable cardiac stimulating device 10 is increased.

The minimal additional circuitry required to implement the present invention is depicted generally in FIG. 1 as parametric data measurement circuitry 42. Although many different types of parametric data may be acquired and stored in accordance with the principles of the present invention, for purposes of illustration, the following description will focus on parametric data pertaining to the lead system 16 and to the battery 18.

Occasionally, due to wear or physical trauma, defects may develop in the lead system 16—which could adversely affect the operation of the implantable cardiac stimulating device 10, if not corrected. For example, a defect in the lead insulation (not shown) on a particular lead could create a short circuit. An opening in the insulation of a unipolar lead (not shown) results in a short circuit between the lead and the surrounding tissue, which could cause a stimulation pulse to be applied to an inappropriate location within the patient's body. A defect in the insulation of a bipolar lead (not shown) may produce a short circuit between the two lead conductors. In either case, a short circuit may prematurely deplete the battery 18 and cause the implantable cardiac stimulating device 10 to fail. A lead impedance measurement taken when a short circuit condition is present would reveal the problem, because the lead impedance would be unusually low.

Lead impedance can also become too high—due to a lead fracture or a change in the quality of the connection of the lead system 16 to the heart 14. If the lead impedance is too high, the pacing circuitry 12 will not be able to properly measure the patient's IEGM, and thus may not apply stimulation pulses at appropriate times. Moreover, the stimulation pulses that are applied to the patient's heart 14 may be rendered ineffective, because the high impedance of the lead system 16 will attenuate the applied pulses. A serious lead fracture can create an open circuit, completely severing the electrical connection between the implantable cardiac stimulating device 10 and the patient's heart 14.

Because the integrity of the lead system 16 is critical to the proper functioning of the implantable cardiac stimulating device 10, the medical practitioner will typically instruct the implantable cardiac stimulating device 10 to take and transmit lead impedance measurements during follow-up examinations. However, lead impedance measurements taken during follow-up examinations may not alert the medical practitioner to problems which only intermittently present themselves. Also, any recent trends relating to lead integrity which occur between follow-up visits are not available for review by the medical practitioner.

In addition to measuring lead impedance during follow-up examinations, the medical practitioner generally also evaluates the condition of the battery 18. The batteries used in implantable cardiac stimulating devices generally have internal impedances that increase as the batteries deplete. Some implantable cardiac stimulating devices are designed so that an increased internal battery impedance slows the stimulation pulse rate by a detectable, but physiologically negligible amount. By measuring the decrease in the stimulation pulse rate of these devices during follow-up visits, the physician can estimate when the battery will be exhausted.

However, this approach to evaluating remaining battery life is limited, because the medical practitioner is not provided with potentially useful information that is available between follow-up visits. For example, in some situations, battery reserves may begin to deplete more rapidly than expected. Indeed, an extremely pronounced upward trend in internal battery impedance is usually a reliable indicator that it is time to replace the battery 18. But without having the benefit of internal battery impedance measurements taken between follow-up visits, such a trend may be difficult for the medical practitioner to detect.

In response to above-described difficulties associated with the conventional practice, the present invention provides for the acquisition and storage of parametric data between follow-up examinations. The types of parametric data measured, and the frequency of the data measurements (e.g., daily, weekly, or monthly), may be programmed by the medical practitioner using the programmer/analyzer 26. Certain types of useful parametric data are derived from other data that are directly measured. For example, lead impedance may be derived from measurements of stimulation pulse voltage and stimulation pulse current, and internal battery impedance may be derived from battery voltage and battery current measurements.

Parametric data measurements are initiated at the appropriate intervals by the control circuitry 20. When it is time to take a parametric data measurement, the control circuitry 20 causes the parametric data measurement circuitry 42 to measure the parameter of interest. Through the connection to the pacing circuitry 12, the parametric data measurement circuitry 42 can acquire pulse voltage and pulse current measurements. The parametric data measurement circuitry 42 can also take measurements of battery voltage and battery current (although the connections are not shown in FIG. 1).

The parametric data measurements taken by the parametric data measurement circuitry 42 are communicated to the control circuitry 20, which in turn can do several things with the data. The control circuitry 20 can store the direct parametric data measurements (e.g., pulse voltage, pulse current, battery current, or battery voltage) in the memory 22. Over time, the memory 22 accumulates a number of measurements for each data type, from which trends in the data and intermittent anomalies may be observed. The control circuitry 20 can also derive other useful types of parametric data (such as lead impedance and internal battery impedance) from the direct data measurements, and then store the derived parametric data in the memory 22. If desired, the control circuitry 20 can also consolidate parametric data measurements by statistically processing the data. This may be useful if the size of the memory 22 poses a limitation on the amount of parametric data that can be stored.

To review the parametric data collected between follow-up visits, the medical practitioner uses the programmer/analyzer 26 to instruct the implantable cardiac stimulating device 10 to transmit the stored data. When the control circuitry 20 receives the instruction, it retrieves the parametric data from the memory 22, and telemetrically transmits the data to the programmer/analyzer 26 via the telemetry circuit 40. The control unit 28 of the programmer/analyzer 26 receives the data via the telemetry head 36, and the control unit 28 then stores the data in the memory 30.

Once the parametric data are stored in the memory 30, the medical practitioner can manipulate the data in a variety of ways to learn about the operating characteristics of the implantable cardiac stimulating device 10. For example, the medical practitioner can issue a command via the user interface 34 to cause the parametric data to be displayed on the display unit 32 as an X-Y graph. The parametric data can also be presented as a histogram, or even as a simple data listing. Statistical calculations can also be performed by the programmer/analyzer 26 (in addition to any performed by the implantable cardiac stimulating device 10), if so desired.

Figure 2:
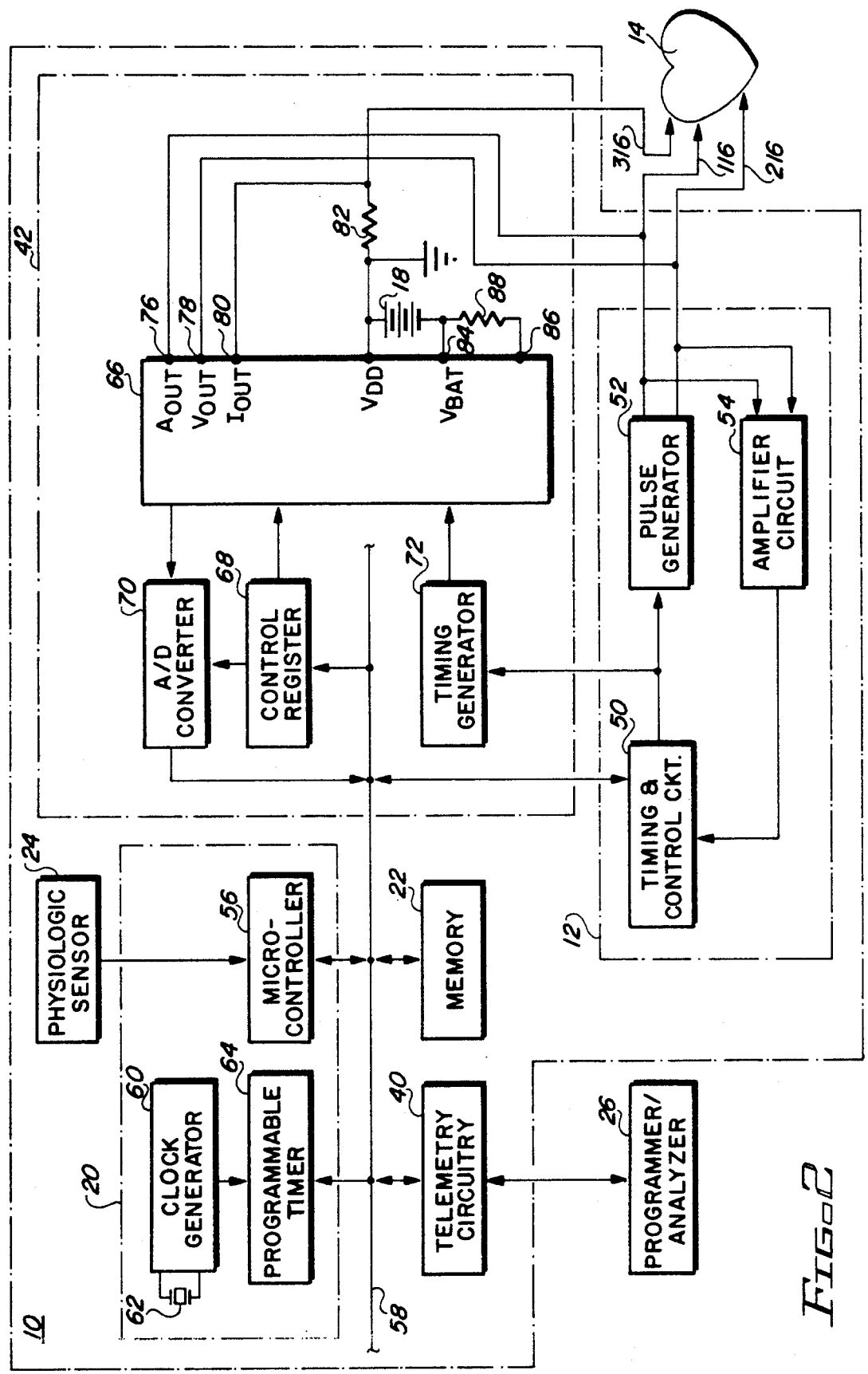
FIG. 2 is a detailed block diagram of the implantable cardiac stimulating device shown in FIG. 1 in accordance with the principles of the present invention.

Referring now to FIG. 2, the implantable cardiac stimulating device 10 is depicted in greater detail to further illustrate the principles of the present invention. In FIG. 2, the pacing circuitry 12 is shown to include a timing and control circuit 50, a pulse generator 52, and an amplifier circuit 54. The amplifier circuit 54 receives the patient's IEGM through the lead system 16 (FIG. 1), which in FIG. 2 is shown to include a first electrode 116 connected to the patient's right atrium (not shown) and a second electrode 226 connected to the patient's right ventricle (not shown). The lead system 116 (FIG. 1) also includes a ground electrode 316. Alternatively, in a bipolar system, separate ground electrodes (not shown), instead of the single ground electrode 316, may be delivered to the heart 14 in separate leads along with the first and second electrodes 116 and 216. In a unipolar system, the ground electrode 316 may be the conductive enclosure (not shown) of the implantable cardiac stimulating device 10, and stimulation pulses may be delivered between each of the electrodes 116 and 216 and the ground electrode 316. Indeed, any suitable lead system configuration may be used in accordance with the principles of the present invention.

The timing and control circuit 50 receives a signal representative of cardiac activity from the amplifier circuit 54, and uses the signal to determine whether stimulation pulses are required. When the timing and control circuit 50 determines that stimulation pulses should be administered to the heart 14, it sends a control signal to the pulse generator 52, which responds by delivering a stimulation pulse to the heart 14 via the lead system 16 (FIG. 1) (i.e., between one of the first and second electrodes 116 and 216 and the ground electrode 316). The timing and control circuit 50 may be programmed to operate in any of variety of pacing modes— including single or dual chamber pacing, single or dual chamber sensing, or combinations thereof.

As mentioned above, the pacing circuitry 12 can operate autonomously for delivering stimulation pulses to the heart 14. However, the implantable cardiac stimulating device 10 includes the control circuitry 20 to enhance its therapeutic capabilities. In FIG. 2, the control circuitry 20 is shown to include a microcontroller 56 which communicates with various other components of the implantable cardiac stimulating device 10—including the memory 22, the telemetry circuitry 40, and the timing and control circuitry 50—via an eight bit communication bus 58. The microcontroller 56 can influence the delivery of stimulation pulses by the pacing circuitry 12 in a variety of ways, for example, by causing the timing and control circuit 50 to change the maintained heart rate in response to a signal from the physiologic sensor 24.

The control circuitry 20 also includes a clock generator 60 which is driven by an oscillator 62. A programmable timer 64 monitors a clock signal generated by the clock generator 60 to determine the intervals at which parametric data measurements are to be made. At the appropriate intervals, the programmable timer 64 interrupts the microcontroller 56, which in turn controls the acquisition and storage of parametric data, as described in greater detail below.

FIG. 2 also provides details for the parametric data measurement circuitry 42—including a data acquisition circuit 66, a control register 68, an analog to digital (A/D) converter 70, and a timing generator 72. The data acquisition circuit 66 includes several input terminals for receiving signals representative of the parametric data of interest. In this embodiment, the data acquisition circuit 66 provides an $A_{OUT}$ terminal 76 through which the stimulation pulse voltage applied to the right atrium via the first electrode 116 is sensed, a $V_{OUT}$ terminal 78 through which the stimulation pulse voltage applied to the right ventricle via the second electrode 216 is sensed, and an $I_{OUT}$ terminal 80 through which a signal representative of the stimulation pulse current is sensed. More precisely, the stimulation pulse current can be derived by measuring the potential that appears across a resistor 82 (having a known resistance value) during the application of a stimulation pulse to the heart 14. Advantageously, the signals received by these three terminals may be used to compute the impedances of the various electrodes of the lead system 16 (FIG. 1).

In this embodiment, the data acquisition circuit 66 also includes input terminals for receiving signals representative of parametric data pertaining to the battery 18. (In FIG. 2, the battery 18 is shown connected only to the data acquisition circuit 66, but it should be understood that the battery 18 supplies other power consuming components of the implantable cardiac stimulating device 10.) The data acquisition circuit 66 provides a $V_{BAT}$ terminal 84 through which the potential of the battery 18 is sensed, and an $I_{BAT}$ terminal 86 through which a signal representative of the current provided by the battery 18 is sensed. More precisely, the battery current can be derived by measuring the potential that appears across a resistor 88 (having a known resistance value). Advantageously, the signals received by these two terminals may be used to compute the internal impedance of the battery 18, which is indicative of remaining battery life.

Of course, other types of parametric data may be measured in accordance with the principles of the present invention. For example, the data acquisition circuit 66 can be modified to acquire parametric data pertaining to the operation of various physiologic sensors, such as the physiologic sensor 24 described above.

The data acquisition circuit 66 preferably includes multiplexer circuitry (not shown) and at least two sample and hold circuits (not shown), which may be conventional. One of the sample and hold circuits is preferably dedicated to sampling the signal representative of the stimulation pulse current (i.e., the potential across the resistor 82 sensed at the $I_{OUT}$ terminal 80). The other sample and hold circuit is selectively coupled to any of the other input terminals to measure the other types of parametric data sensed by the data acquisition circuit 66. Of course, other configurations are possible as are appropriate for a particular application.

The selection of parametric data to be measured by the data acquisition circuit 66 is made in accordance with control information stored in the control register 68. The control information is provided to the communication bus 58 by the microcontroller 56 when a parametric data measurement is to be taken. After the selected measurement is made, the microcontroller 56 provides additional control information to the control register 68, which causes the data acquisition circuit 66 to send the stored measurement to the A/D converter 70. In response, the A/D converter digitizes the analog parametric data measurement and sends the digitized parametric data to the microcontroller 56. The microcontroller 56 can derive additional parametric data (such as lead impedance and internal battery impedance) from the directly measured data, and then store various combinations of the parametric data in the memory 22. And as described above, the microcontroller 56 can perform statistical calculations on the parametric data measurements, and store the results in the memory 22.

For parametric data measurements which do not need to be synchronized to the delivery of stimulation pulses, the timing of the data measurements can be easily controlled by the control circuitry 20. However, the present invention contemplates parametric data measurements which require such synchronization and accordingly, the timing generator 72 is provided.

When the timing and control circuit 50 determines that a stimulation pulse should be administered, it generates a trigger signal that is provided to pulse generator 52 which responsively delivers the stimulation pulse to the heart 14 via the lead system 16 (FIG. 1). The stimulation pulse is typically applied to the heart 14 for the duration of the trigger signal which is usually about 100 µs to about 1.5 ms in duration. The timing generator 72 also experiences the trigger signal and in response, it provides a narrow timing pulse of approximately 50 µs to the data acquisition circuit 66. The timing pulse is delayed slightly with respect to the leading edge of the trigger signal, to ensure that the parametric data measurement is taken while the stimulation pulse is being applied to the heart 14. Thus, the actual data measurement time may deviate somewhat from the measurement interval determined by the programmable timer 64.

Figure 3:
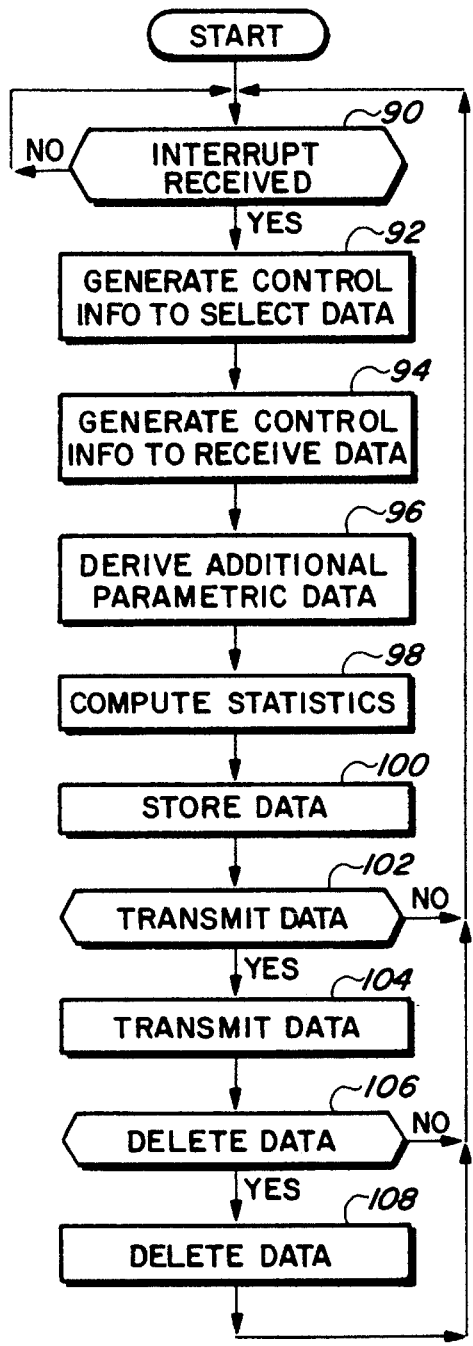
FIG. 3 depicts a logic flow diagram representative of a portion of a control program executed by a microcontroller of the implantable cardiac stimulating device shown in FIG. 1, for controlling the acquisition and storage of parametric data in accordance with the principles of the present invention.

Referring now to FIG. 3, a logic flow diagram representing a portion of a control program for the microcontroller 56 of FIG. 2 in accordance with a preferred embodiment of the present invention is described. A test 90 is depicted to represent the time during which the microcontroller 56 (FIG. 2) waits for an interrupt signal from the programmable timer 64 (FIG. 2). When an interrupt signal is received, the microcontroller 56 (FIG. 2) generates control information at a step 92. The control information, which is sent to the control register 68 (FIG. 2) via the communication bus 58 (FIG. 2), defines the particular type of parametric data to be measured by the data acquisition circuit 66 (FIG. 2). The data measurement is taken when the data acquisition circuit 66 (FIG. 2) receives a timing pulse from the timing generator 72 (FIG. 2).

After the parametric data measurement is taken, the microcontroller 56 (FIG. 2) generates additional control information at a step 94, which is also provided to the control register 68 (FIG. 2). This control information causes the A/D converter 70 (FIG. 2) to digitize the analog parametric data measurement. The digitized parametric data measurement is then sent to the microcontroller 56 (FIG. 2) via the communication bus 58 (FIG. 20.

At a step 96, the microcontroller 56 (FIG. 2) uses the directly measured parametric data to derive other useful types of parametric data (e.g., lead impedance and internal battery impedance). Then, at a step 98, the microcontroller 56 (FIG. 2) performs statistical calculations on the parametric data (the statistics may be performed on recently acquired parametric data as well as parametric data acquired during previous measurement intervals). Various types of statistical calculations can be performed, including mean, variance, maximum value, and minimum value. At the step 98, the microcontroller 56 (FIG. 2) may also perform statistical calculations for the purpose of consolidating data. For example, if several months pass between follow-up visits, it may be desirable to statistically consolidate older parametric data measurements and delete the individual measurement from which the statistics are derived, perhaps on a monthly basis. In this manner, the medical practitioner could evaluate recent trends (because the most recent parametric data measurements would not yet be deleted) and still be able to review statistical data representative of the performance of the implantable cardiac stimulating device 10 (FIG. 2) from earlier months.

After the statistical calculations are performed, at a step 100, the microcontroller 56 (FIG. 2) stores the parametric data (whether directly measured or derived, as appropriate) in the memory 22 (FIG. 2). At this step, the microcontroller 56 (FIG. 2) also stores the results of any statistical calculations performed at the step 98.

At a test 102, the microcontroller 56 (FIG. 2) determines whether a request to transmit the stored parametric data has been received from the programmer/analyzer 12 (FIG. 2) via the telemetry circuitry 40 (FIG. 2). If a request to transmit data has not been received, the microcontroller 56 (FIG. 2) loops back to the test 90, where it waits for the next interrupt signal. Otherwise, at a step 104, the microcontroller 56 (FIG. 2) causes the telemetry circuitry 40 to transmit the parametric data stored in the memory 22 (FIG. 2).

At a test 106, the microcontroller 56 (FIG. 2) determines whether a command to delete any of the stored parametric data has been received. Through the programmer/analyzer 12 (FIG. 2), the medical practitioner can choose to delete all of the stored data, or a selected amount of the data. For example, it may be useful to retain certain monthly statistical information in the memory 22 (FIG. 2) for review at the next follow-up visit along with parametric data collected between the current visit and the next visit. If no command to delete parametric data has been received, the microcontroller 56 (FIG. 2) loops back to the test 90. If such a command has been received, the selected data are deleted at a step 108 before the microcontroller 56 (FIG. 2) loops back to the test 90.

Once the parametric data are transmitted to the programmer/analyzer 12 (FIG. 2), the data can be presented to the medical practitioner in a variety of ways. In some cases, a simple data listing may be appropriate, which may be printed, or displayed on the display unit 32 (FIG. 1). Alternatively, more complex graphical presentations may provide the medical practitioner with a better understanding of the operating characteristics of the implantable cardiac stimulating device 10 (FIG. 2). Such graphical representations may include histograms, charts, and X-Y graphs.

Figure 4:
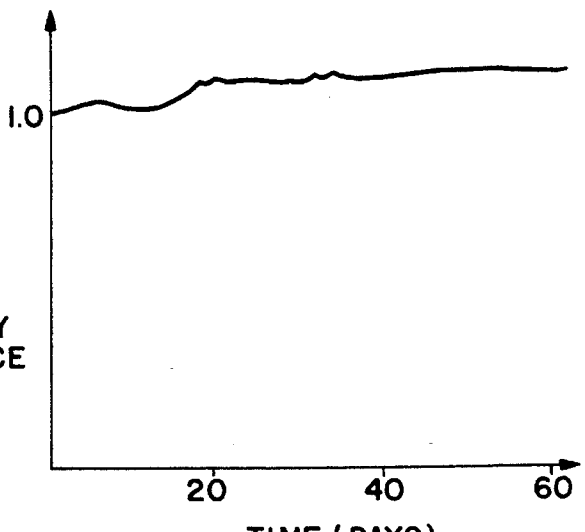
FIG. 4 is an illustrative graphical representation of internal battery impedance plotted as a function of time, derived using parametric data measurements acquired in accordance with the principles of the present invention.

An illustrative X-Y graph which may be particularly useful is shown in FIG. 4. The graph depicts internal battery impedance (derived from the battery voltage and battery current measured by the data acquisition circuit 66 (FIG. 2)) plotted against time. Of course, similar presentations may be provided by the programmer/analyzer 12 (FIG. 2) for other types of parametric data. In addition, the programmer/analyzer 12 (FIG. 2) may be used to perform additional statistical calculations not performed by the microcontroller 56 (FIG. 2).

Thus, a system and method for measuring and storing parametric data pertaining to the operating characteristics of an implantable medical device are provided. One skilled in the art will appreciate that the present invention can be practiced by other than the described embodiments, which are presented for purposes of illustration and not of limitation, and the present invention is limited only by the claims that follow.

What is claimed is:

1. An implantable cardiac stimulating device having telemetry means for communicating with an external displaying means, said implantable cardiac stimulating device comprising:

pulse generating means for generating stimulation pulses, said pulse generating means having a plurality of varying parametric data associated therewith;

means for measuring said plurality of varying parametric data;

memory means for storing said plurality of parametric data measurements;

first control means for autonomously triggering said measuring means at predetermined intervals; and second control means for transferring the plurality of stored parametric data from said memory means to said telemetry means and for triggering said telemetry means to communicate said stored parametric data to said external displaying means.

2. The implantable cardiac stimulating device of claim 1, further comprising:

a battery for supplying a battery voltage and a battery current to said pulse generating means, said battery having an impedance associated therewith, said battery impedance being derived from said battery voltage and battery current, said battery impedance providing an indication of battery longevity;

at least one stimulation lead, coupled to the pulse generating means, through which said stimulation pulses are delivered to cardiac tissue, said stimulation pulses having a stimulation pulse voltage and a stimulation pulse current associated therewith, said stimulation lead having a lead impedance associated therewith which may be derived from said stimulation pulse voltage and stimulation pulse current, said lead impedance providing an indication of lead integrity; and wherein said means for measuring includes means for measuring direct and derived parametric data, said direct parametric data comprising at least one of said battery voltage, said battery current, said stimulation pulse voltage, and said stimulation pulse current, and said derived parametric data comprising at least one of said battery impedance or lead impedance;

whereby at least said derived parametric data is indicative of said implantable cardiac stimulating device longevity, stability, and efficacy.

3. The implantable cardiac stimulating device of claim 2, further comprising:

computational means for calculating statistical data utilizing said stored parametric data; and wherein said memory means further includes means for storing said statistical data;

whereby said statistical data is indicative of said implantable cardiac stimulating device longevity, stability, and efficacy.

4. The implantable cardiac stimulating device of claim 1, wherein said means for measuring comprises:

means for detecting a cardiac event; and means for synchronizing measurement of said varying parametric data to said cardiac event.

5. The implantable cardiac stimulating device of claim 1, wherein said first control means comprises programmable timer means for causing said first control means to trigger said measuring means at said predetermined intervals.

6. An implantable medical device having telemetry circuitry for communicating with an external programmer/analyzer, said implantable medical device comprising:

data measurement circuitry for measuring parametric data pertaining to said implantable medical device after said device has been implanted in body tissue;

memory for storing said parametric data; and control circuitry coupled to said data measurement circuitry and said memory, said control circuitry having a first, a second and a third control signal as an output, said first control signal being for triggering said data measurement circuitry to measure said parametric data at predetermined intervals, said second control signal being for triggering said memory to store said parametric data measured by said data measurement circuitry, and said third control signal being for triggering said telemetry circuitry to communicate said parametric data stored in said memory to said programmer/analyzer when a request for said stored parametric data is received from said programmer/analyzer via said telemetry circuit.

7. The implantable medical device of claim 6, wherein:

said implantable medical device further comprises a battery for supplying a battery voltage and a battery current; and said data measurement circuitry comprises input terminals for receiving signals representative of said battery voltage and battery current, wherein said battery voltage and battery current are types of parametric data measured by said data measurement circuitry.

8. The implantable medical device of claim 7, wherein:

said control circuitry includes computing circuitry which receives as inputs said measurements of battery voltage and battery current to compute internal battery impedance values; and said memory includes means for storing said internal battery impedance values.

9. The implantable medical device of claim 6, wherein:

said implantable medical device further comprises a pulse generator for generating stimulation pulses, said stimulation pulses having a pulse voltage and a pulse current; and said data measurement circuitry comprises input terminals for receiving signals representative of said pulse voltage and said pulse current, wherein said pulse voltage and pulse current are types of parametric data measured by said data measurement circuitry.

10. The implantable medical device of claim 9, wherein:

said implantable medical device includes an implantable stimulation lead having a lead impedance value;

said stimulation pulses are applied to living tissue via said implantable stimulation lead;

said control circuitry includes computing circuitry which receives as inputs said measurements of pulse voltage and pulse current to compute said lead impedance value; and said memory includes means for storing said lead impedance value.

11. The implantable medical device of claim 9, wherein said data measurement circuitry comprises timing means for causing said data measurement circuitry to synchronize said parametric data measurements with said stimulation pulses provided by said pulse generator.

12. The implantable medical device of claim 6, wherein:

said control circuitry includes computing circuitry which receives a plurality of said parametric data measurements as inputs and produces as an output statistical calculations on said parametric data measurements; and said memory includes means for storing results of said statistical calculations.

13. A method of acquiring parametric data pertaining to operating characteristics of an implantable medical device, said implantable medical device having telemetry circuitry for communicating with an external programmer/analyzer, said method comprising the steps of:

autonomously measuring said parametric data at predetermined intervals using data measurement circuitry contained within said implantable medical device;

storing said parametric data in a memory contained within said implantable medical device;

receiving instructions from said programmer/analyzer via said telemetry circuitry to transmit said parametric data to said programmer/analyzer; and transmitting said parametric data to said programmer/analyzer in response to said received instructions.

14. The method of claim 13, further comprising the steps of:

receiving said parametric data transmitted by said implantable medical device using said programmer/analyzer; and displaying said diagnostic data on a display of said programmer/analyzer.

15. The method of claim 14, wherein said step of displaying said parametric data comprises the step of displaying said parametric data in the form of an X-Y graph as a function of the times at which said parametric data were measured.

16. The method of claim 13, wherein:

said measuring step comprises measuring signals representative of battery voltage and battery current of a battery contained within said implantable medical device; and said storing step comprises storing said measurements of battery voltage and battery current in said memory.

17. The method of claim 16, wherein:

said method further comprises the step of computing internal battery impedance values from said measurements of battery voltage and battery current; and said storing step comprises storing said internal battery impedance values in said memory.

18. The method of claim 13, wherein:

said measuring step comprises measuring signals representative of pulse voltage and pulse current of stimulation pulses provided by a pulse generator contained within said implantable medical device; and said storing step comprises storing said measurements of pulse voltage and pulse current in said memory.

19. The method of claim 18, wherein:

said method further comprises the step of computing from said measurements of pulse voltage and pulse current, lead impedance values of a lead used to apply said stimulation pulses to living tissue; and said storing step comprises storing said lead impedance values in said memory.

20. The method of claim 18, further comprising the step of synchronizing said parametric data measurements with said stimulation pulses provided by said pulse generator.

21. The method of claim 13, wherein:

said method further comprises the step of performing statistical calculations on said parametric data measurements; and said storing step comprises storing results of said statistical calculations in said memory.

22. An implantable cardiac stimulation system, comprising:

pulse generating means for generating stimulation pulses, said pulse generating means having a plurality of parametric data associated therewith, said plurality of parametric data varying over time;

measuring means for automatically measuring said plurality of parametric data at predetermined intervals;

storing means for storing said plurality of parametric data measurements;

external display means for displaying said plurality of parametric data measurements;

telemetry means for communicating said plurality of parametric data measurements to said external displaying means; and control means for transferring the stored parametric data from said storing means to said telemetry means and for triggering said telemetry means to communicate said stored parametric data to said external displaying means.

23. The implantable cardiac stimulating system of claim 22, further comprising a battery for supplying a battery voltage and a battery current to said pulse generating means, said battery having an impedance associated therewith, wherein said measuring means comprises:

means for measuring direct parametric data, said direct parametric data comprising at least said battery voltage and said battery current; and means for determining derived parametric data from said direct parametric data, said derived parametric data comprising at least said battery impedance.

24. The implantable cardiac stimulating system of claim 22, further comprising at least one stimulation lead coupled to the pulse generating means and through which said stimulation pulses are delivered to cardiac tissue, said stimulation pulses having a stimulation pulse voltage and a stimulation pulse current associated therewith, said stimulation lead having a lead impedance associated therewith, wherein said measuring means comprises:

means for measuring direct parametric data, said direct parametric data comprising at least said stimulation pulse voltage and said stimulation pulse current; and means for determining derived parametric data from said direct parametric data, said derived parametric data comprising at least lead impedance.

25. The implantable cardiac stimulating system of claim 22, further comprising:

computing means for calculating statistical data utilizing said stored parametric data;

wherein said memory means further includes means for storing said statistical data; and wherein said external displaying means includes means for displaying said statistical data.

26. The implantable cardiac stimulating system of claim 22, wherein said external displaying means further comprises:

graphical means for graphically displaying said stored parametric data as a function of time so that trends are displayed.

* * * * *